United States Patent [19]

Englehardt et al.

[11] Patent Number: 4,894,325

[45] Date of Patent: Jan. 16, 1990

[54] HYBRIDIZATION METHOD FOR THE DETECTION OF GENETIC MATERIAL

[75] Inventors: Dean L. Englehardt; Elazar Rabbani, both of New York, N.Y.

[73] Assignee: Enzo Biochem, Inc., New York, N.Y.

[21] Appl. No.: 5,327

[22] Filed: Jan. 15, 1987

Related U.S. Application Data

[63] Continuation of Ser. No. 653,816, Sep. 24, 1984, abandoned, which is a continuation-in-part of Ser. No. 605,022, Apr. 27, 1984, abandoned.

[51] Int. Cl.[4] .................. C12Q 1/68; G01N 33/552; G01N 33/546
[52] U.S. Cl. ........................................ 435/6; 935/78; 435/803; 436/527; 436/520; 436/533
[58] Field of Search .................. 435/5, 6, 34, 7, 803; 436/501, 508, 518, 520, 527, 533; 935/77, 78, 81

[56] References Cited

U.S. PATENT DOCUMENTS

| | | | |
|---|---|---|---|
| 4,298,685 | 11/1981 | Parikh et al. | 436/530 |
| 4,334,017 | 6/1982 | Plotkin et al. | 436/501 X |
| 4,358,535 | 11/1982 | Falkow et al. | |
| 4,376,110 | 3/1983 | David et al. | |
| 4,376,165 | 3/1983 | Hornby et al. | 435/188 |
| 4,486,539 | 12/1984 | Ranki et al. | |
| 4,510,244 | 4/1985 | Parks et al. | |
| 4,554,088 | 11/1985 | Whitehead et al. | 436/526 |
| 4,563,417 | 1/1986 | Albarella et al. | 935/78 |
| 4,699,876 | 10/1987 | Libeskind | 435/5 |
| 4,724,202 | 2/1988 | Dattagupta et al. | |
| 4,731,325 | 3/1988 | Palva et al. | 935/77 X |
| 4,749,647 | 6/1988 | Thomas et al. | 435/6 |
| 4,755,458 | 7/1988 | Rabbani et al. | 935/78 X |

FOREIGN PATENT DOCUMENTS 0070685 1/1983 European Pat. Off.
0070687 1/1983 European Pat. Off.
2027031 2/1980 United Kingdom.

OTHER PUBLICATIONS

Munns, T. W. et al., Progress in Nucleic Acid Research and Molecular Biology 24: 10: 9–114, 1980.
Dunn; A. R. et al., Methods in Enzymology 65: 468–476, 1980.
Martinell; J. Proc. Natl. Acad. Sci. USA 78:5056–5060 (1981).
"Monoclonal Antibody Specific for Double-Stranded DNA: A Non-Radioactive Probe Method for Detection of DNA Hybridization" by C. Huang et al., pp. 257–270 in Rapid Detection and Identification of Infectious Agents, Academic Press, Inc. (1985).
Program of International Symposium on "Rapid Detection and Identification of Infectious Agents" at University of California, Berkeley, Naval Biosciences Laboratory, 7–10, Oct. 1983.

*Primary Examiner*—John W. Rollins
*Assistant Examiner*—Jeremy M. Jay
*Attorney, Agent, or Firm*—Charles J. Herron; Serle I. Mosoff

[57] ABSTRACT

This invention provides methods for the detection of a target genetic material having a desired base sequence or gene. Also disclosed are methods for the detection of mutations. Also provided are components for use in such methods.

The methods are based upon techniques which utilize two labeled single stranded polynucleotide segments which are complementary to the same or the opposite strands of the target genetic material. The methods of the invention result in the formation of a double hybrid and/or multihybrid.

15 Claims, 3 Drawing Sheets

POLYNUCLEOTIDE PROBE SYSTEM

DENATURED TARGET GENETIC MATERIAL

HYBRIDIZATION TO FORM THE MULTIHYBRID

HYBRIDIZATION METHOD FOR THE DETECTION OF GENETIC MATERIAL

CROSS-REFERENCED TO RELATED APPLICATION

This is a continaution of application Ser. No. 653,816, filed Sept. 24, 1984, entitled "HYBRIDIZATION METHOD FOR THE DETECTION OF GENETIC MATERIAL" now abandoned, which is a continuation-in-part of application Ser. No. 605,022, filed Apr. 27, 1984.

BACKGROUND OF THE INVENTION

Nucleic acid hybridization assays are used as a tool for the detection and identification of a target genetic material such as DNA or RNA. Such detection and identification can be for a specific DNA or RNA sequence or specific gene or a point mutation or deletion of a DNA or RNA sequence or gene. A number of techniques exist to carry out such assays. (see *Methods In Enzymology*, Vol. 68, R. Wu (Ed) pp. 379–469, 1979; and Dunn, A. R., and Sambrook J., *Methods In Enzymology*, vol 65; Part 1, pp. 468–478, 1980). One of the most w. used procedures is called the Southern blot filter hybridization methods (Southern, E., J. Mol. Biol. 98, 503, 1975). This procedure is usually used to identify a particular DNA fragment separated from a mixture of DNA fragments by electrophoresis. The procedure is generally carried out by isolating a sample of DNA from some microorganism. The isolated DNA is subjected to a restriction endonuclease disgestion and electrophoresed on a gel (agarose, acrylamide, etc.). When the gel containing the separated DNA fragments is put in contact (blotted with a nitrocellulose filter sheet or diazotized paper, etc.), the fragments are transferred and become bound to the nitocellulose sheet. The gel-transfer nitrocellulose sheet containing the DNA fragments is then heated to denature the DNA. At this point the sheet is treated with a solution containing a denatured labeled DNA probe and hybridization is allowed to take place. The unhybridized labeled DNA probe is then washed away. The label of the DNA probe is then detected.

It is known to carry out a homogeneous hybridization assay based upon non-radiative energy transfer. This hybridization assay system utilizes a chemiluminescent catalyst and an absorber/emitter moiety. The system involves the use of two polynucleotide reagent strands in such a way that the hybridization assays carried out are in a homogeneous fashion. This means that the target polynucleotide sequence can be detected and identified in solution without the need to carry out any immobilization procedures. The method comprises contacting the target genetic material, under hybridization conditions, with first and second single stranded polynucleotide reagent segments which are complementary to substantially mutually exclusive portions of the target single stranded polynucleotide. The first reagent segment has a chemiluminescent catalyst and the second reagent segment has an absorber/emitter moiety positioned such that, upon hybridization with the target single stranded polynucleotide, the chemiluminescent catalyst and absorber/emitter moiety are close enough in proximity to permit non-radiative energy transfer. The single stranded polynucleotide sample is then contacted with chemiluminescent reagents effective for causing light emission in the presence of the chemiluminescent catalyst. The quantity of light emitted by the absorber/emitter moiety is then measured by an appropriate instrument which thereby indicates the presence of the sample single stranded polynucleotide. This method is disclosed in European Patent Application Publication No. 0 070 685, published Jan. 26, 1983.

SUMMARY OF THE INVENTION

This invention provides methods for the detection of a target genetic material having a desired base sequence or gene. Also disclosed are methods for the detection of mutations, such as a point mutation or the deletion of a gene or base. Also provided are components for use in such methods.

The methods based upon techniques which utilize two labeled single stranded polynucleotide segments which are complementary to the same or the opposite strands of the target genetic material. The methods of the invention result in the formation of a double hybrid and/or a multihybrid, defined hereinbelow.

The method of detection of the double hybrid and the multihybrid is dependent upon the choice of label.

Each single stranded polynucleotide segment can be either part of the same polynucleotide segment i.e., one probe which comprises two polynucleotide segments of interest or can be two separate polynucleotide segments, i.e., two probes with each probe comprising a polynucleotide segment of interest. The label of each probe can be a particle, a moiety which is capable of generating a signal, either directly, e.g., a radioactive label, or indirectly, e.g., an enzyme-linked system or a system wherein each label alone can not create a signal, but when such labels are brought into contact a signal can be generated.

BRIEF DESCRIPTION OF THE FIGURES

The invention will be better understood by reference to the attached Figures wherein.

DETAILED DESCRIPTION OF THE INVENTION

Figure 1:
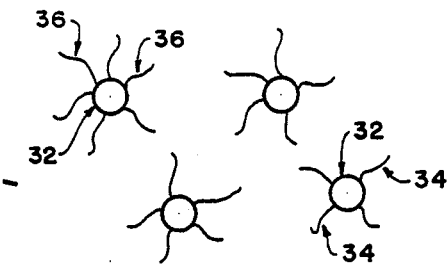
FIG. 1 represents a preferred scheme for the assay system within the invention. The denatured target genetic material 10 comprises the (+) strand 12 and the (−) strand 14. The (−) strand 14 comprises region 16, region 18 and region 20. The polynucleotide probe system 30 comprises a mixture of particles 32. Each particle 32 has attached thereto numerous (+) single stranded polynucleotide segments, 34 or 36. Single stranded polynucleotide segment 34 is complementary to region 16 and single stranded polynucleotide segment 36 is complementary to region 20. When the method of the invention is carried out numerous single stranded polynucleotide segments 34 hybridize to region 16 and numerous single stranded polynucleotide segments 36 hybridize to region 20 to form the multihybrid 40.
Figure 1:
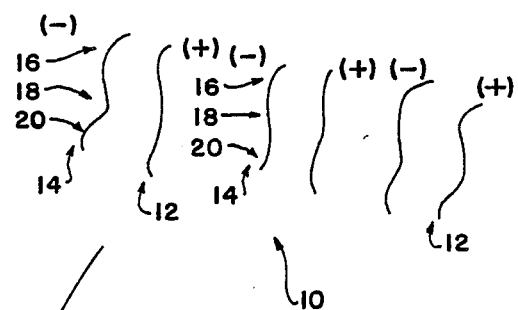
Figure 1:
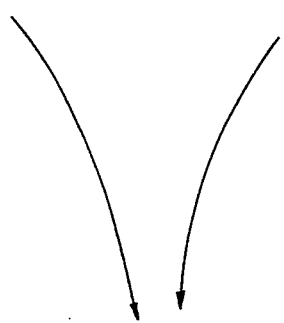
Figure 1:
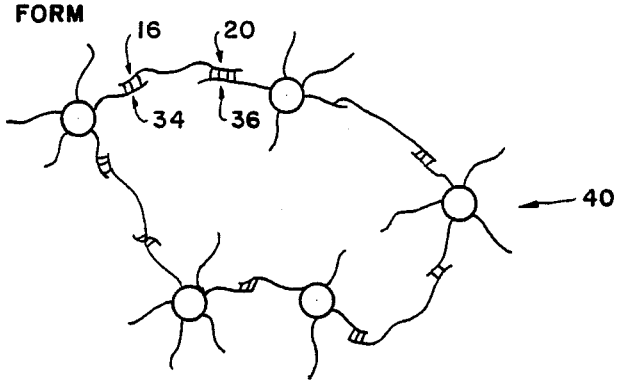
Figure 2:
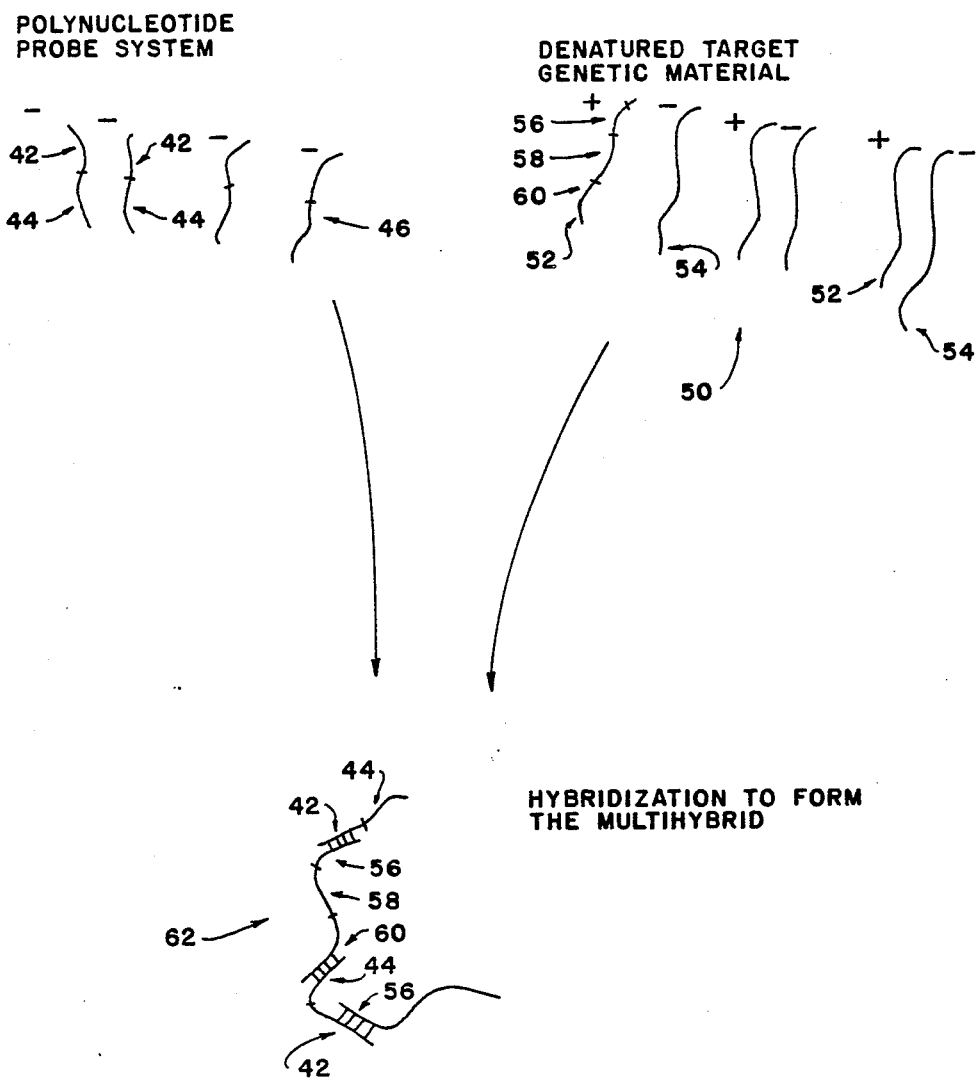
FIG. 2 represents another embodiment of the invention wherein the two single stranded polynucleotide segments, 42 and 44, are part of the same (+) polynucleotide segment 46. The denatured target genetic material 50 comprises the (+) strand 52 and (−) strand 54. The (+) strand 52 comprises region 56, region 58 and region 60. Single stranded polynucleotide segments 42 and 44 are complementary to regions 56 and 60, respectively. When the method of the invention is carried out numerous single stranded polynucleotide segments 42 hybridize to region 56 and numerous single stranded polynucleotide segments 44 hybridize to region 60 to form the multihybrid 62.
Figure 3:
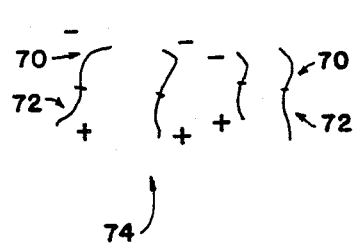
FIG. 3 represents another embodiment of the invention wherein the two single stranded polynucleotide segments, 70 and 72, are part of the same polynucleotide segment 74. The denatured target genetic material 80 comprises The (+) strand strand 82 and the (−) strand 84. The (+) strand 82 comprises region 86, region 88 and region 90. The (−) strand 84 comprises region 92, region 94 and region 96. Single stranded polynucleotide segments 70 and 72 are complementary to regions 86 and 96, respectively. When the method of the invention is carried out numerous single stranded polynucleotide segments 70 and 72 hybridize to regions 86 and 96, respectively, to form the multihybrid 98.
Figure 3:
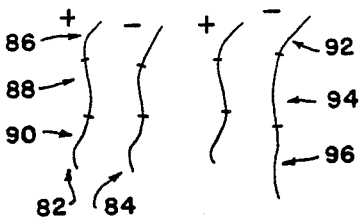
Figure 3:
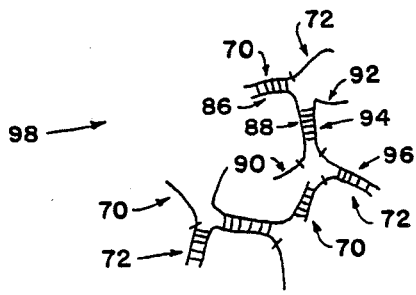

This invention provides methods for the detection of genetic material such as DNA or RNA. The methods are based upon techniques which utilize two single stranded polynucleotide segments, with each segment comprising a label. Each single stranded polynucleotide segment is complementary to the same or the opposite strand of the target genetic material. When the two single stranded polynucleotide segments are separate segments, there are two polynucleotide probes and when the two single stranded polynucleotide segments are part of the same polynucleotide segment there is one polynucleotide probe, albeit such one polynucleotide probe comprises two single stranded polynucleotide segments of interest. Thus, when the method of the invention is carried out, a double hybrid is formed which comprises two polynucleotide probes joined by their hybridization to the target genetic material (hereinafter referred to as the "double hybrid"). Also, depending upon the choice of label and whether or not the two single stranded polynucleotide segments are a separate polynucleotide segments or are part of the same polynucleotide segment, the double hybrid can be interconnected so as to form a multihybrid (hereinafter referred to as the "multihybrid"). Both the double hybrid and the multihybrid are detectable.

The double hybrid or the multihybrid, and therefore, the target genetic material, is detectable by one of three methods. The method that can be utilized to detect the double hybrid or multihybrid is dependent upon what kind of label is utilized. First, the double hybrid or multihybrid is detectable by the fact of the formation of the double hybrid or multihybrid itself. The double hybrid or multihybrid is directly detectable as a precipitate or a glob or a glob-like structure. This precipitate or glob or glob-like structure itself separates from the polynucleotide probes which did not form the double hybrid or multihybrid. This result can be obtained when each label is, for example, a particle. This is an agglutination hybridization assay.

The second method that can be utilized to detect the double hybrid or multihybrid is obtained when one of the labels is, for example, a particle and one of the labels is an entity that is capable of creating a signal, e.g., a radioactive label or an enzyme linked system. The detection of the double hybrid or multihybrid by this method may require a separation step to separate the double hybrid or multihybrid from those polynucleotide probes which comprise such entities that are capable of creating a signal which have not formed the double hybrid or multihybrid. Otherwise, such unhybridized polynucleotide probes may create a signal which can result in a false positive result. This is commonly referred to as "background".

The third method in which the double hybrid or multihybrid is detectable is if each label alone is neither capable of creating a signal itself, either directly or indirectly, nor is a particle, but when the double hybrid or multihybrid is formed, each label of the double hybrid or multihybrid can come into contact and thereby create a signal.

The method of the invention can be carried out with great simplicity. The target genetic material is denatured, i.e., rendered in single stranded form, in an appropriate solvent system by conventional techniques such as by heating or adding a strong base. The target genetic material is then contacted with the polynucleotide probe system under hybridization conditions. Butit should be noted that the polynucleotide probe system can be added to the solvent system either before, during or after the denaturation of the target genetic material. It is preferred to add a vast excess of the polynucleotide probe system. This enhances the likelihood that the double hybrid or multihybrid will be formed. It is essential that the polynucleotide probes be singee stranded when they contact the target genetic material. Otherwise, the polynucleotide probes will not be able to hybridize with the target genetic material. However, the polynucleotide probe can be in double stranded form and then denatured and then be utilized to contact the target genetic material. This denaturation can be carried out in the solvent system at the same time the target genetic material is being denatured. It should be noted that it is preferred that when the label of the polynucleotide probe is a particle, that the polynucleotide segment be in single stranded form. Otherwise, when the target genetic material is contacted by the polynucleotide probe under hybridizing conditions, the double strands of the polynucleotide probe can easily renature. This can be carried out by, for example, deriving the single stranded polynucleotide segment from a single stranded DNA or RNA phage, separating the (+) and (−) polynucleotide segments and attaching either the (+) o, the (−) polynucleotide segment to the particle or attaching both the (+) and (−) polynucleotide segments to the particle in such a fashion that they can not hybridize to each other of the same or different particles.

The double hybrid or multihybrid can now be detected. However, depending on the choice of label and whether or not each polynucleotide probe comprises a single stranded polynucleotide segment which is a separate polynucleotide segment or part of the same polynucleotide segment, those polynucleotide probes which did not form the double hybrid or multihybrid may then have to be separated from those polynucleotide probes which did form the double hybrid or multihybrid.

As disclosed hereinabove, the two single stranded polynucleotide segments can be either two separate polynucleotide segments, i.e., a two polynucleotide probe system, or can be part of the same polynucleotide segment, i.e., a one polynucleotide probe system.

The Two Single Stranded Polynucleotide Segments As Two Separate Segments

The two single stranded polynucleotide segments can be two separate polynucleotide segments, with each polynucleotide segment being labeled. In this embodiment of the invention there are two polynucleotide probes. Each single stranded polynucleotide segment is complementary to substantially mutually exclusive portions of the same or the opposite strands of the target genetic material.

When each single stranded polynucleotide segment is complementary to opposite strands of the target genetic mate,ial it is preferred that each single stranded polynucleotide segment be totally mutually exclusive. This prevents the possibility of each single stranded polynucleotide segment from hybridizing to each other when the method of the invention is carried out, thus resulting in a background signal. Also, when each single stranded polynucleotide segment is complementary to opposite strands of the target genetic material it is essential that each single stranded polynucleotide segment be selected such that when each is hybridized to its complementary strand of the target genetic material there is at least one sequence of both strands of the target genetic material that is available to hybridize to each other. This is due to that when the method of the invention is carried out the opposite strands of the target genetic material will hybridize to each other to form the double hybrid.

When the method of the invention is carried out with each single stranded polynucleotide segment capable of hybridizing with the same strand of the target genetic material, each segment can hybridize to a separate sequence of the same strand of the target genetic material which results in the formation of the double hybrid. This embodiment of the invention is preferred because only two hybridizations are required for the formation of the double hybrid.

As disclosed hereinabove, the double hybrid can be detected by one of three methods, depending upon the choice of the label of each polynucleotide probe.

In a preferred embodiment in the practices of the present invention each polynucleotide probe is labeled with a particle. When the methods of the invention are carried out with the label of each polynucleotide probe being a particle, the resulting double hybrid comprises two particles which is separable from those polynucleotide probes labeled with a particle which did not form the double hybrid. (Also, as a less preferred embodiment, more than one particle can be attached to each polynucleotide probe). However, it is particularly preferred that each particle comprise numerous single stranded polynucleotide segments. This results in the formation of the multihybrid due to the particles bridging the double hybrids. The multihybrid forms a precipitate or glob or glob-like structure which itself is much more readily detectable than the double hybrid.

The particle can be a macroparticle or a microparticle wherein a microparticle is in solution or preferably a suspension in the solvent system. The particles can be made from a variety of materials including glass, nylon, polymethacrylate, polystyrene, polyvinylchloride, latex, chemically modified plastic, rubber, red blood cells, a polymeric material or biological cells. Such particles may be readily obtained from or manufactured from material obtained from a variety of sources including, for instance, Polysciences, Inc., Pennsylvania.

The single stranded polynucleotide segment can be attached to the particle by any technique. For example, the, single stranded polynucleotide segment can be covalently attached to the particle, attached by nonspecific binding or attached by means of the formation of a complex of the particle and the single stranded polynucleotide segment. Complex formation is the noncovalent binding between complementary portions of two molecules. For example, the particle can be coated with avidin and the single stranded polynucleotide segment can be labeled with biotin wherein such segment will then complex with the avidin. Essentially any ligand and receptor can be utilized to complex the polynucleotide segment with the particle. Suitable ligands and receptors include a polynucleotide sequence to be recognized by its complementary sequence, an antibody portion to be recognized by its corresponding antigen, a hormone to be recognized by its receptor, an inhibitor to be recognized by its enzyme, a co-factor portion to be recognized by a co-factor enzyme binding site, a binding ligand to be recognized by its substrate, e.g., biotin-avidin (and any analogs or derivitives thereof) or sugar-lectin, with the biotin-avidin system being preferred. When the single stranded polynucleotide segment is attached to the particle by complex formation it is preferred to add the particle to the solvent system after the target genetic material is contacted by the single stranded polynucleotide segment.

It is preferred that the single stranded polynucleotide segment be attached to the particle through a moiety. This enhances the ability of the single stranded polynucleotide segment to hybridize with the target genetic material. Suitable moieties are essentially any moiety including, for example, synthetic and natural polymers and oligomers, and preferably polynucleotides. Preferably, each single stranded polynucleotide segment has terminally attached thereto an oligonucleotide tail which is not complementary to the target genetic material. Each single stranded polynucleotide segment can then be attached to the particle through the oligonucleotide tail by any of the techniques described hereinabove, except for the nonspecific binding.

The second method in which the target genetic material can be detected is wherein one of the polynucleotide probes is labeled with a particle and the other polynucleotide probe is labeled with a moiety that is capable of generating a signal.

The particle can be any of those particles described hereinabove.

The moiety that is capable of creating a signal encompasses virtually any of the signal generating systems used in the prior art and any system to be developed in the future. It comprises a moiety which generates a signal itself, e.g., a dye, a radioactive molecule, a chemiluminescent material, a fluorescent material or a phosphorescent material, or a moiety which upon further reaction or manipulation will give rise to a signal, e.g., an enzyme linked system.

Suitable enzymes that can be utilized to create a signal are essentially any enzyme that is capable of generating a signal when treated with a suitable reagent. Preferred enzymes are horseradish peroxidase, alkaline phosphatase, glucose oxidase, peroxidase, acid phosphatase and beta galactosidase. Such enzymes are preferred because they are very stable, yet highly reactive.

This method is a less preferred embodiment of the invention. This is due to the fact that during the detection step of the method of the invention it is essential to carry out a procedure to separate the polynucleotide probes which comprise a moiety that is capable of creating a signal that did not form the double hybrid from those polynucleotide probes which did form the double hybrid. This separation can be carried out by sedimentation, centrifugation or filtration or other known techniques.

The third method in which the target genetic material can be detected is wherein each single stranded polynucleotide segment has a label attached thereto wherein when the double hybrid is formed each label of each single stranded polynucleotide segment has an affinity or is capable of themselves complexing and then is capable of creating a signal. Neither label of each polynucleotide probe alone is capable of creating a signal.

In this system it is preferred that each of the two labels be attached, either covalently or via complex formation, at one end of each single stranded polynucleotide segment. Thus, it is preferred that the first label be attached in the three prime terminal position of the first single stranded polynucleotide segment add that the second label be attached at the five prime terminal position of the second single stranded polynucleotide segment. Therefore, when the double hybrid is formed, each label will be positioned as close as possible to each other. However, it is particularly preferred that both strands i.e., the (+) and (−) strand of each polynucleotide probe be labeled with the same label. By having both strands of the single stranded polynucleotide segment being labeled with the same label there is no background signal. This is because during the hybridization step of the method of the invention if such polynucleotide probes hybridize to each other, no signal is created.

In this system it is preferred that the label of each polynucleotide probe have an affinity or be able to form a complex. It is believed that this assists in increasing the proximity of the two labels. This will result in a stronger signal. Such affinity or complex formation can be naturally occurring, e.g., an apoenzyme is one label and such apoenzyme's cofactor, as the other label. In this system a signal can be created by adding a suitable reagent, but such signal is only created if the apoenzyme and its cofactor form a complex. The affinity or complex can also be artificially created. For example, one label can be a chemiluminescent catalyst and the other label can be an absorber/emitter moiety wherein each of such labels has attached thereto oligonucleotides that are complementary. Such oligonucleotides will hybridize to each other and keep the chemiluminescent catalyst and absorber/emitter moiety in extremely close proximity which will render such system efficacious. This system can be carried out as described in European Patent Application Publication No. 0 070 685, published Jan. 26, 1983, the disclosure f which is incorporated herein. All of the ligand and receptors disclosed hereinabove can be utilized to create the artificial affinity.

In another aspect of the third method of detection of the target genetic material numerous labels can be attached throughout each single stranded polynucleotide segment. It is believed that the attachment that numerous labels to such segments increases the likelihood that when the double hybrids form the labels of each of such segments will come into contact with each other. Thus, the signal will then be able to be created. Such labels can be attached to the single stranded polynucleotide segments by methods described in co-pending. co-assigned European Patent Applications Publication Nos. 0 063 879, published Nov. 3, 1982 and 0 097 373, published Jan. 4, 1984, the disclosures of which are incorporated herein. These European Patent Application Publications are derived from U.S. patent application Ser. No. 225, 223, now abandoned filed Apr. 17, 1981 and U.S. patent application Ser. No. 391, 440 now abandoned , filed June 23, 1982, respectively. It is preferred to attach such labels via complex formation. This permits one to add the labels after the complex has been formed Otherwise, such labels, due to their bulk may inhibit each polynucleotide probe from hybridizing with the target genetic material. It should be noted that it is essential that when the label is added after the single stranded polynucleotide segments have been permitted to hybridize with the target genetic material that the complex utilized to attach the label should be different for each polynucleotide probe. This prevents both labels from being attached to the same single stranded polynucleotide segment which would create a background signal.

In yet another aspect of the third method in which the target genetic material can be detected is wherein one of the labeled single stranded polynucleotide segments is fixed to a matrix, such as nitrocellulose, nylon, polystyrene, polyvinylchloride or a transparent or translucent matrix such as glass. This system has the advantage of specificity; only the target genetic material will be fixed to the matrix. Thus, some genetic material that may cause a background signal will not be fixed to the matrix.

In yet another embodiment of the present invention there is utilized one polynucleotide probe and, rather than utilizing the second polynucleotide probe, an antibody to double stranded genetic material. (In this embodiment of the invention only the (+) strand or (−) strand of the polynucleotide probe can be present). The antibody can be labeled with a particle, such as those described hereinabove, which results in the formation of the multihybrid. The antibody can also be labeled with a moiety which is capable of creating a signal, such as those described hereinabove. The polynucleotide probe can be labeled with a particle or a moiety that is capable of creating a signal, however, it is essential that at least either or both the polynucleotide probe or the antibody be labeled with a particle. Also, it is believed, as a less preferred embodiment, that the antibody need not be labeled, but is solely utilized to bridge the polynucleotide probes, which forms the precipitate, glob or glob-like structure which itself is detectable.

In yet another embodiment of this aspect of the present invention, i.e., two single stranded polynucleotide segments as separate segments, there is provided a capture assay.

In this embodiment of the invention the first polynucleotide segment is labeled with a particle, a moiety which is capable of generating a signal, either directly, e.g. a radioactive label, or indirectly, e.g. an enzyme linked system or a system wherein the label alone cannot create a signal, but when such label is contacted with another label a signal can be generated. All of such labels as disclosed hereinabove can be utilized.

The second polynucleotide segment is labeled with a different moiety than the first polynucleotide segment or, preferably, is unlabeled. A different moiety in the context of this embodiment of the present invention exists whenever an effective method exists that can discriminate between the two moieties. In addition, the second polynucleotide segment comprises a moiety that is capable of complex formation.

The moiety that is capable of forming a complex is utilized to form a complex with a moiety that is attached to a matrix, such as nitrocellulose, nylon, polystyrene, polyvinylchloride or a transparent or translucent matrix such as glass. Essentially any ligand and receptor can be utilized to make he complex formation.

Suitable ligands and receptors include a oligo or polynucleotide sequence to be recognized by its complementary sequence, an antigen portion to be recognized by its corresponding antibody, a hormone to be recognized by its receptor, an inhibitor to be recognized by its enzyme, a co-factor portion to be recognized by a co-factor enzyme binding site, a binding ligand to be recognized by its substrate, e.g., biotin-avidin (and any analogs or derivitives thereof) or sugar-lectin, with the biotin-avidin system being preferred. When an oligo or polynucleotide sequence is utilized, it is preferred that the oligo or polynucleotide sequence be a homopolymer or oligomer or a repeating copolymer or oligomer. It is believed that the complex formation by a ligand and receptor is of much higher affinity, efficiency and speed than the complex formation of the target genetic material and each single stranded polynucleotide segment.

When the capture assay is carried out, it is believed that the double hybrid or multi hybrid is first formed and then is "captured" by the matrix. Thus, when the method of the invention is carried out, those first polynucleotide segments that were not "captured" by the matrix can be separated from those that did by washing them from the matrix. In a preferred embodiment of this embodiment of the present invention, the target genetic material is contacted with the first and second polynucleotide segments so as to form the double hybrid or multihybrid and then the matrix is contacted with the double hybrid or multihybrid. This assures that the hybrid or multihybrid will be formed before the second polynucleotide segment is captured by the matrix.

The Two Single Stranded Polynucleotide Seqments Are Part Of The Same Polynucleotide Segment The two single stranded polynucleotide segment can be part of the same polynucleotide segments. In this embodiment of the present invention there is only one polynucleotide probe, but such polynucleotide probe comprises at least two single stranded polynucleotide segments of interest. The single stranded polynucleotide probe can comprise a label, although a label is not essential, but only preferred. Each single stranded polynucleotide segment can be complementary to the same strand or the opposite strands of the target genetic material.

When each single stranded polynucleotide segment is complementary to opposite strands of the target genetic material it is preferred that no portion of each segment be complementary. Also, when each single stranded polynucleotide segment is complementary to opposite strands of the target genetic material it is essential that each single stranded polynucleotide segment be selected such that when each is hybridized to its complementary strand of target genetic material there is at least one sequence of both strands of the target genetic materials that is available to hybridize to each other. Thus when the method of the invention is carried out the opposite strands of the target genetic material will hybridize to each other to form the double hybrid, which is the only structure that can form.

When each single stranded polynucleotide segment is complementary to the same strand of the target genetic material the segments must be noncontiguous. The noncontiguity can be created by, for example, placing a "spacer" sequence between each single stranded polynucleotide segment which is not complementary to the target genetic material or, preferably, by selecting each single stranded polynucleotide segment from distant portions of the target genetic material. It is this noncontiguity that permits the formation of the double hybrid. A portion of the strand of the target genetic material can hybridize with the first single stranded polynucleotide segment and then the unhybridized portion of such target strand can hybridize to the second single stranded polynucleotide segment of another polynucleotide probe, thus resulting in the double hybrid. This embodiment is less preferred because it is possible for the strand of target genetic material which hybridized to the first single stranded polynucleotide segment to hybridize to the second single stranded polynucleotide segment of the same probe, thus forming no double hybrid. This can be minimized by increasing the length of the noncontiguity of each of the single stranded polynucleotide segments.

In this embodiment of the invention the multihybrid can be formed without attaching more than one single stranded polynucleotide probe to a label. The target genetic material, rather than the label, joins the double hybrids to form the multihybrids. Thus, a precipitate or glob or glob-like structure can be formed without a label. It is preferred that the polynucleotide probe comprise a label. The label renders the multihybrids more easily detectable because the label can decrease the solubility of the polynucleotide probe. As with the embodiment of the invention wherein the two single stranded polynucleotide segments are separate segment, the label of the polynucleotide probe can be a particle Preferably, many probes are attached to each particle. This results in the formation of an even larger multihybrid. The same particles as described hereinabove can be utilized. Also, the single stranded polynucleotide probe can be attached to the particle by techniques as described hereinabove.

The label can be an entity other than a particle. The label can be any moiety that decreases the solubility of the polynucleotide probe. For example, the label can be a DNA binding protein that binds DNA. This can be carried out by adding such binding proteins before, during or after the target genetic material is contacted with the polynucleotide probe.

The multihybrid can be rendered more easily detectable by utilizing on a portion of the probes a label which is a moiety which is capable of creating a signal. The attachment of such label permits one to amplify the signal generated by the formation of the multihybrid In this embodiment it is preferred, but not essential, that during the detection step the polynucleotide probe which comprises a moiety which can create a signal but does not form the multihybrid is separated from those which did form the multihybrid. Such separation step can be carried out very simply due to the fact of the formation of such multihybrid. It is believed that the polynucleotide probes which did not form part of the multihybrid can just be poured off to separate them from the multihybrid. The moieties that can be utilized to create a signal are the same as those described hereinabove.

The target genetic material can be detected by utilizing a portion of the polynucleotide probes labeled with a first label and a portion of the polynucleotide probes labeled with a second label wherein the first and second label are not capable of creating a signal themselves, but when they contact each other they are able to create a signal. It is preferred that about half of the polynucleotide probes be labeled with the first label and about half with the second label. This maximizes the amount of signal that can be created.

The same first and second labels can be utilized as described hereinabove.

INHIBITION ASSAY

The target genetic material can also be detected by utilizing an inhibition hybridization assay based upon the principles of the invention, i.e., the inhibition of the formation of the double hybrid or multihybrid is measured. This can be carried out with the two polynucleotide probe system. However, it is essential that each single stranded polynucleotide segment be selected such that they are complementary to not only the target genetic material, but also complementary to each other. Also, in this embodiment of the invention one of the polynucleotide probes can be fixed to a matrix, such as a nitrocellulose filter, rather than being labeled. Also, it should be noted that in this embodiment of the invention an inhibition capture assay canbe carried out which is based upon the principles of th capture assay. All of the labels described hereinabove can be utilized. Also, such labels can be attached to the single stranded polynucleotide segment by the techniques described hereinabove.

The method can be carried out with great simplicity. The target genetic material is denatured in an appropriate solvent system, i.e., rendered single stranded, by conventional techniques. The target genetic material is then contacted with the polynucleotide probe system and a "blocking" agent under hybridization conditions. The blocking agents are either, but not both, the (+) or the (−) sequences of polynucleotides which are complementary to either the (+) or (−) strand of the target genetic material, but are not complementary to each of the single stranded polynucleotide segments. The blocking agent prevents each strand of the target genetic material from joining the two polynucleotide probes. However, it should be noted that if the target genetic material is single stranded, e.g., mRNA, then no blocking agent is required. The detection of the presence of the double hybrid or multihybrid can now be accomplished. If no double hybrids or multihybrids are formed or fewer double hybrids or multihybrids are formed, then the target genetic material is present. Also, it should be noted that this method is most efficacious when the concentration of the target genetic material is equal to or greater than the concentration of the polynucleotide probe system.

The assay can also be carried out wherein instead of detecting the presence of the target genetic material by the inhibition of the formation of the double hybrid or multihybrid, the detection of the target genetic material is determined by the hybridization of one of the polynucleotide probes to the target genetic material. For example, the first polynucleotide probe, which need not be labeled, can be fixed to a matrix in an appropriate first solvent system. A vast excess of this polynucleotide probe, as compared to the second polynucleotide probe and target genetic material is utilized. In a second solvent system the target genetic material is denatured, i.e., rendered into to single stranded to form. The second polynucleotide probe is then utilized to contact the target genetic material under hybridization conditions. (A blocking agent, if necessary, can be utilized herein for the same reasons as described hereinabove). It is essential that the label of this polynucleotide probe be a moiety which itself is capable of creating a signal, e.g., a radioactive label. Suitable moieties are those described hereinabove. The components of the second solvent system, which are still under hybridization conditions, are then transferred to the first solvent system. Thus, under hybridizing conditions, any or all of the second polynucleotide probe which has not hybridized to the target genetic material can hybridize to the first polynucleotide probe, which is fixed to the matrix. Thus, there will remain in the solvent in solution the second polynucleotide probe which is hybridized to the target genetic material. This can be detected by creating a signal with the label of the second nucleotide probe. This assay can also be carried out by means other than utilizing the first polynucleotide probes for separating the second polynucleotide probes that are hybridized to the target genetic material from those that are not. Any suitable means can be used. For example, an enzyme, such as S1 or micrococcal nuclease, that destroys single stranded genetic material can be utilized to destroy the second polynucleotide probes that did not hybridize with the target genetic material. Also, an antibody to double or single stranded DNA or RNA can be utilized to do the separation by fixing such antioody to a matrix in the first solvent system. Also, bouyant density centrifugation or hydroxylappatite chromatography can be utilized for such separation.

DETECTION OF MUTATIONS

The method of the invention can also be utilized to detect a genetic mutation such as a point mutation, an inversion and both a large (greater than about 15 nucleotides) and a small (less than about 15 nucleotides) deletion or insertion, and a genetic change leading to an alteration of a restriction enzyme cleavage site, a restriction enzyme polymorphism site. This can be carried out by utilizing the methods of the invention which result in the formation of the double hybrid or multihybrid. However, it is essential that at least one of the single stranded polynucleotide segments comprise a sequence that is substantially complementary, and preferably completely complementary, to the site of the mutation or the site restriction enzyme polymorphism site, whichever is appropriate. It is also preferred that such segment comprise the flanking nucleotides of the appropriate site. After the formation of the double hybrid or the multihybrid, the double hybrid or multihybrid can be contacted with an appropriate restriction enzyme that can cleave at least one position on a double hybrid if the site is present or absent, depending on the choice of polynucleotide probe. Such cleavage results in the breaking of the double hybrid, and therefore, the multihybri if the multihybrid is present. The breaking of th hybrid or the multihybrid is detectable.

The choice of the single stranded polynucleotide probe to be utilized is dependent upon whether a restriction enzyme site that identifies the mutant is present or absent in the mutated genetic material. If the restriction enzyme site is present, then it is essential that the single stranded polynucleotide probe contain the restriction enzyme site sequence. If the restriction enzyme site is absent, then it is essential that the single stranded polynucleotide probe contain the sequence for the restriction enzyme site that identifies the mutant, which site is present in the wild type genetic material.

In another aspect of the invention when at least one of the single stranded polynucleotide probes comprises a sequence complementary to the restriction enzyme site sequence that identifies the mutant that is present in the mutant target genetic material rather than the wild type target genetic material, such a probe can comprise many restriction enzyme site sequences that identify the mutant, each of which is complementary to restriction enzyme site sequences that identify the mutant from different mutant target genetic materials. Thus, one assay can be utilized to detect the existance of at least one of many possible mutations. It is not necessary to carry out a separate assay to determine the existance of each mutation in this case.

Another embodiment of this aspect of the invention is wherein in the polynucleotide probe system of the invention wherein there are two polynucleotide probes, one of the polynucleotide probes is fixed to a matrix, such as a nitrocellulose filter or a transparent or translucent surface. It is not essential that the fixed polynucleotide probe be labeled, but it is essential that the other polynucleotide probe, which preferably contains the restriction enzyme site that identifies the mutation, be labeled with a moiety that is capable of creating a signal, such as those described hereinabove. When the method of the invention is carried out, the double hybrid can be formed, which is fixed to the matrix. The portion of the target genetic material that did not form the double hybrid should be separated from those strands which did form the double hybrid, unless the signal is only capable of formation if the double hybrid is formed. The double hybrid is then contacted with an appropriate restriction enzyme which results in breaking the double hybrid, thereby releasing the moiety that is capable of creating a signal. The disappearance of the moiety that is capable of creating a signal from the matrix or the presence of such moiety in the solution of the solvent system can be detected.

A less preferred embodiment of this aspect of the invention is a method which utilizes only one polynucleotide probe. Such probe contains the restriction enzyme site that identifies the mutation and a label which is a moiety that is capable of creating a signal, such as those described hereinabove. The polynucleotide probe is then fixed to a matrix, such as those described hereinabove, such that the portion of the single stranded polynucleotide segment that comprises the mutant target genetic material is between the portion of the single stranded polynucleotide segment which is fixed to the matrix and the portion of the single stranded polynucleotide segment which comprises the moiety that is capable of creating a signal. The polynucleotide probe is then contacted with the target genetic material, which has been rendered single stranded, under hybridization conditions. The strands of the target genetic material that did not hybridize are separated from those which did hybridize, unless the signal is only capable of formation if the hybrid is formed. The resulting hybrid is then contacted with the appropriate restriction enzyme. The moiety that is capable of creating a signal is then released. The disappearance of such moiety from the matrix or the presence of such moiety in the solution of the solvent system can be detected.

Yet another aspect of this invention is a method for the detection of large mutations, i.e., mutations involving deletions or insertions into the nucleotide sequence of greater than about 15 nucleotides. This method utilizes a polynucleotide probe which comprises a polynucleotide sequence that is complementary to the nucleotide sequence of the insertion or the deletion.

In the practice of this aspect of the invention it is preferred that a positive assay for deletions is observed when the probe does not react with the mutant genetic material and for insertions a positive assay is observed when the probe is shown to react with the mutant genetic material.

The method can be carried out by any conventional hybridization assay, by the methods of this invention or by any hybridization assay to be developed in the future. Utilizing such probe provides an easy method for the detection of large mutations.

EXAMPLE I

A simple demonstration of the feasibility of detecting a solubilized target genetic material by the formation of the multihybrid was performed using poly rA linked to agarose beads as the probe and poly rU as the soluble target genetic material. In one assay, titration of a suspension of poly rA - agarose with increasing amounts of poly rU was evaluated by microscopic examination of the resulting suspensions. In each suspension the number of agarose beads that was observed to be overlapping or touching another bead were counted. With increasing amounts of poly rU, the number of said complexes increased indicating that poly rU brought poly rA-linked beads into measurably close proximity of one another.

In a separate experiment, poly rA agarose beads were suspended in buffer on microscope slides with (a) no addition, (b) with added poly rA, and (c) with added poly rU.

Because of the low complexity of the nucleic acid sequences, it was immediately observed that the distribution of beads in (c) was different from that in (a) and (b). In (c), the beads floated together as a mass while in (a) and (b) the beads appeared to float freely of each other. This demonstrated that in some circumstances a macroscopic agglomeration of particles can be obtained in such a detection system.

EXAMPLE II

This example discloses a method for labeling a first single stranded polynucleotide segment that has poly dG at the 5' end with fluorescein and a second single stranded polynucleotide segment that has poly dG at the 3' end with microperoxidase. Also, the flourescein containing moiety had attached thereto a thymidine trimer and the microperoxidase has attached thereto an adenine trimer.

STEP I: Formation of 5-(3-aminopropyl) deoxyuridine (Propylamino-dU)

Uridine is reacted with mercuric chloride (5 mmol) at pH 5.0. 5-mercurichloride-dU so produced is reacted with acrylonitrile and lithium tetrachloro-palladiate in methanol yielding 5-(2-cyanoethyl) which is reduced by hydrogenation at 3 atmospheres in the presence of 10% palladium on charcoal in methanol.

STEP II: Formation of 5-(N-fluoroscenyl-3-aminopropyl)-dU (fluorescein-dU)

Propylamine-dU is reacted with fluorescein isothiocyanate at pH 8.5. The product is purified by cellulose chromatography.

STEP III: Formation of 3'-benzoyl-fluorescein-dU

Fluorescein-dU is reacted with di-p-dimethoxytrityl chloride in dry pyridine. The 5'-dimethoxytrityl fluorescein dU is purified by silica gel chromatography and acetylated with benzoyl chloride in dry pyridine. 5'- dimethoxytrityl-3'-benzoyl-fluorescein dU is purified by silica gel chromatography. The compound is detritylated by dissolving in methanol: chloroform, 3:7 (v/v) containing 2% benzene sulfonic acid. The product is purified by silica gel chromatography.

Step IV: Formation of
(dA)$_3$—(fluorescein—dU)—3'—OH (dA)$_3$ fully protected for use in phosphotriester oligonucleotide synthesis was deblocked in anhydrous pyridine with triethylamine. Solvent, amine and acrylonitrile are removed by rotary evaporation. The residue is dissolved in dry pyridine along with 3'-benzoyl-fluorescein-dU (0.8 mole equivalent) and triisopropylbenzene sulfonyl tetrazole. The crude product is concentrated by evaporation, dissolved in chloroform and washed with bicarbonate. The oligonucleotide is detritylated by treatment with 2% benzene sulfonic acid in 7:3 chloroform: methanol, chromatographed on preparative TLC and (silica gel) and deblocked by treatment of 50° C. in concentrated ammonia hydroxide. After evaporation of ammonia the product is purified by HPLC reverse phase chromatography.

STEP V: Formation of
5'—OH—(dA)$_3$—(Fluorescein-dU)-(dG)$_n$3'—OH
(5'labeled-oligo dG)

(dA)$_3$—(fluorescein-dU)-3'—OH (1 ug), lmM dGTP (2.5 ul), terminal transferase (25 u) and 0.01 m CoCl$_2$ (5 ul) are incubated in 0.2 m potassium cacodylate buffer pH 7.0 containing 1mM mercaptoethanol (final vol. 40 ul) at 37° for 1 hour. The reaction is stopped by heating at 65° C. for 5 minutes. The oligo dG product was purified on oligo dC cellulose.

STEP VI: Formation of (T)$_3$-propylamino-dU

Propylamino-dU is blocked with 2-(tert-butoxy carbononyloxyimino)-2-phenylacetonitrile (BOC-ON). This compound is reacted successively with dimethoxy tritylchloride and benzoyl chloride as previously described for the preparation of 3'-benzoyl fluorescein-dU. The trityl group is selectively cleaned by hydrogenolysis at atmosphere pressure in the presence of 5% palladium on charcoal. The N-BOC-3'-acetyl aminopropyl-dU is condensed with protected (T)$_3$-oligonucleotide, deblocked and purified as described for the preparation of (dA)$_3$-fluorescein-dU.

STEP VII: Preparation of
oligo-dG-(8-aminohexyladenosine)

Oligo dG (100 ug.) is reacted with 8-aminohexyladenosine-5'-triphosphate in the presence of terminal transferase in cacodylate buffer as previously described. The oligo-dG is isolated by oligo-dC-cellulose chromatography.

STEP VIII: Preparation of microperoxidase coupled to oligo sG (8-aminohexyladenosine)

Oligo dG-(8-aminohexyladenosine) (100 ug.) and microperoxidase (10 mg) is reacted with 1 mg. 1-ethyl-3-(3-dimethylamino propyl) carbodiimide (EDAC) in 100 ul. 0.1M sodium chloride. The reaction is dialyzed and the coupled product isolated by oligo-dC chromatography.

STEP IX: Preparation of microperoxidase coupled to (T)3 and oligo dG

Microperoxidase coupled oligo dG (mixed with oligo dG) is reacted with (T)$_3$-propylamino-dU in the presence of EDAC. The product is purified by successive chromatography on oligo-dC-cellulose and oligo-dA-cellulose.

What is claimed is:

1. A method for the detection of single-stranded target genetic material comprising the steps of:
   (a) contacting, under conditions permissive of hybridization, said target genetic material with
      (i) a first polynucleotide probe comprising a first partic to which is attached a plurality of first single-stranded polynucleotide segments complementary to a first portion of said target genetic material, and
      (ii) a second polynucleotide probe comprising a second particle having attached thereto a plurality of second single-stranded polynucleotide segments complementary to a second portion of said target genetic material;
   (b) permitting hybridization of said first polynucleotide segments to said first portion of target genetic material and said second segments to said second portion of target genetic material, said hybridizations resulting in agglutination; and
   (c) detecting said agglutination.

2. The method of claim 1, wherein at least one of said first and second particles is a microparticle.

3. The method of claim 1, wherein said second polynucleotide probe further comprises a moiety that is capable of creating a signal.

4. The method of claim 1, wherein said first and second particles are microparticles.

5. A method for the detection of single-stranded target genetic material comprising the steps of:
   (a) contacting, under conditions permissive of hybridization.
      (i) an unhybridized portion of a first strand of target genetic material with a first polynucleotide probe comprising a first particle to which is attached a plurality of first single-stranded polynucleotide segments complementary to said first single strand of target genetic material;
      (ii) an unhybridized portion of a second strand of target genetic material with a second polynucleotide probe comprising a second particle having attached thereto a plurality of second single-stranded polynucleotide segments complementary to said second single strand of target genetic material; and
      (iii) an unhybridized portion of said first and said second strand of target genetic material;
   with the provisos that:
      said first and second single stranded polynucleotide segments are not capable of hybridizing to each other:
      hybridization of said first polynucleotide segment to said unhybridized portion of said first strand of target genetic material and hybridization of said second polynucleotide segment to said unhybridized portion of said second strand of target genetic material do not prevent at least a portion of said first strand of target genetic material from being available to hybridize with at least a portion of said second strand of target genetic material, (b) permitting the hybridization of
(1) said first polynucleotide segment to said unhybridized portion of said first strand of target genetic material,
(2) said second polynucleotide segment to said unhybridized portion of said second strand of target genetic material, and
(3) said unhybridized portion of said first strand of target genetic material and said unhybridized portion of said second strand of target genetic material, the foregoing hybridizations occurring in any order; said hybridizations resulting in agglutination; and (c) detecting such hybridizations by means of the agglutination that occurs.

6. The method of claim 5, wherein at least one of said first and second particles is a microparticle.

7. The method of claim 5, wherein said second polynucleotide probe further comprises a moiety that is capable of creating a signal.

8. The method of claim 7, wherein said first and second particles are microparticles.

9. A method for the detection of single-stranded target genetic material which comprises:

(a) Contacting complementary strands of said target genetic material under conditions permissive of hybridization, with an amount, relative to the amount of target genetic material sufficient to prevent substantial reannealing thereof, of a polynucleotide probe wherein said polynucleotide probe comprises a label attached to a single-stranded polynucleotide segment having a first portion complementary to a first strand of the target genetic material and a second portion complementary to a second strand of the target genetic material, said first strand and said second strand of target genetic material being (I) complementary to each other and (ii) such that when said first portion and said second portion are hybridized to said target genetic material, there is at least one sequence of each of the complementary strands of said target genetic material that is available to hybridize to the other strand;

(b) permitting hybridization thereof resulting in the formation of a detectable multihybrid, and (c) detecting said multihybrid.

10. The method of claim 9 wherein said complementary strands of single-stranded target genetic material are contacted with a polymer formed of repeating units of said polynucleotide probe which comprises a single-stranded polynucleotide segment having a first portion and a second portion wherein said first portion is complementary to a first strand of the target genetic material and said second portion is complementary to a second strand of the target genetic material.

11. The method of claim 9 wherein said polynucleotide probe further comprises a label.

12. The method of claim 11 wherein said label is a particle.

13. The method of claim 12 wherein said particle is a microparticle.

14. The method of claim 13 wherein said microparticle has at least two of said single-stranded polynucleotide segments attached thereto.

15. A method for the detection of a single-stranded target genetic material which comprises (a) contacting, under conditions permissive of hybridization, a sample suspected of containing said target genetic material with
(i) a plurality of first polynucleotide probes comprising a first entity attached to a first single-stranded polynucleotide segment which is hybridizable with a first portion of said target genetic material;
(ii) a plurality of first particles having attached thereto a second entity which is specifically bindable with said first entity;
(iii) a plurality of second polynucleotide probes comprising a third entity and attached thereto a second single-stranded polynucleotide segment hybridizable with a second portion of said target genetic material; and
(iv) a plurality of second particles having attached thereto a fourth entity which is specifically bindable with said third entity;

(b) permitting hybridization of said first and second probes with said target genetic material, binding of said first entity with said second entity and binding of said third entity with said fourth entity so as to form an agglutination complex; and (c) detecting the presence of said target by observing said agglutination complex.

* * * * *